(12) United States Patent
Kochman et al.

(10) Patent No.: US 6,926,683 B1
(45) Date of Patent: Aug. 9, 2005

(54) METHOD FOR REDUCING THE APPEARANCE OF SKIN CELLULITES USING VACUUM RADIANT HEAT AND MECHANICAL MANIPULATION

(75) Inventors: Michael Kochman, Ramsey, NJ (US); Amir Waldman, Moshav Yarqona (IL)

(73) Assignee: Tensor Technologies, LLC, Ramsey, NJ (US)

( * ) Notice: Subject to any disclaimer, the term of this patent is extended or adjusted under 35 U.S.C. 154(b) by 0 days.

(21) Appl. No.: 09/552,586

(22) Filed: Apr. 19, 2000

Related U.S. Application Data

(63) Continuation-in-part of application No. PCT/IL99/00686, filed on Dec. 15, 1999.

(51) Int. Cl.[7] ............................................. A61H 15/02
(52) U.S. Cl. ............................ 601/118; 601/6; 601/15; 601/126; 607/100
(58) Field of Search .................. 601/6, 7, 15, 18, 601/19, 112–113, 118–123, 125, 126–129

(56) References Cited

U.S. PATENT DOCUMENTS

| | | | |
|---|---|---|---|
| 927,125 A * | 7/1909 | Davis ........................... | 601/125 |
| 2,218,443 A | 10/1940 | Tweddle | |
| 2,258,931 A | 10/1941 | Heer et al. | |
| 3,835,844 A * | 9/1974 | Lang ............................ | 128/33 |
| 3,878,837 A * | 4/1975 | Werding ....................... | 128/57 |
| 3,970,078 A * | 7/1976 | Rogers, Jr. ................... | 128/57 |
| 4,086,922 A * | 5/1978 | Henderson .................... | 601/19 |
| 4,292,971 A * | 10/1981 | Smit et al. .................... | 604/23 |
| 4,729,368 A | 3/1988 | Guitay | |
| 4,832,006 A * | 5/1989 | Kirsch .......................... | 128/57 |
| 4,883,047 A | 11/1989 | Guitay | |
| 5,094,225 A * | 3/1992 | Craw ........................ | 128/24.3 |
| 5,336,159 A * | 8/1994 | Cheng .......................... | 601/15 |
| 5,413,587 A * | 5/1995 | Hochstein ................... | 607/100 |
| 5,665,053 A * | 9/1997 | Jacobs .......................... | 601/2 |
| 5,797,859 A * | 8/1998 | Prehodka ..................... | 601/22 |
| 5,830,161 A * | 11/1998 | Cosmano ................... | 601/121 |
| 5,885,232 A | 3/1999 | Guitay | |
| 5,961,475 A * | 10/1999 | Guitay .......................... | 601/7 |
| 6,017,320 A * | 1/2000 | Bleeker et al. ............. | 601/125 |
| 6,196,982 B1 * | 3/2001 | Ball .............................. | 601/6 |
| 6,273,884 B1 | 8/2001 | Altshuler et al. | |
| 6,309,364 B1 * | 10/2001 | Cathaud et al. ................ | 601/7 |
| 6,511,445 B2 * | 1/2003 | Sivan et al. ................... | 601/6 |
| 6,517,499 B1 * | 2/2003 | Pereira ......................... | 601/7 |
| 6,605,080 B1 | 8/2003 | Altshuler et al. | |
| 6,702,766 B2 * | 3/2004 | Guitay .......................... | 601/6 |
| 2002/0151826 A1 * | 10/2002 | Ramey et al. ................. | 601/6 |
| 2004/0236252 A1 * | 11/2004 | Muzzi et al. .................. | 601/1 |

FOREIGN PATENT DOCUMENTS

| | | |
|---|---|---|
| AU | 23845/77 | 10/1978 |
| EP | 0 637 442 | 2/1995 |
| GB | 193 687 | 3/1923 |

* cited by examiner

*Primary Examiner*—Jerome W. Donnelly
*Assistant Examiner*—Victor K. Hwang
(74) *Attorney, Agent, or Firm*—Davidson, Davidson & Kappel, LLC

(57) ABSTRACT

A massaging apparatus that includes at least one massaging element in a housing and extending therefrom for use in manipulating a subject's tissue and further including a radiant heat source.

18 Claims, 3 Drawing Sheets

METHOD FOR REDUCING THE APPEARANCE OF SKIN CELLULITES USING VACUUM RADIANT HEAT AND MECHANICAL MANIPULATION

RELATED APPLICATION

This application is a continuation-in-part of PCT application Ser. No. PCT/IL99/00686 filed on 15 Dec. 1999

FIELD OF INVENTION

The present invention relates to improved devices for use in massaging the human body and more particualrly to massage devices, especially useful and effective for substantially reducing cellulite caused skin deformities.

BACKGROUND OF THE INVENTION

Massage devices are designed to imitate the masseur's hands in manipulating the tissue of the subject undergoing the massage. Massages improve local circulation, muscle tone and relieve physical muscular tension, and therefore, are relaxing. Massaging also has been used in the past in attempting to remove deformities caused by cellulites. Cellulites are lumpy fat deposits that make a person's body look older. When the fat is deposited immediately below the dermis, the connective tissue elasticity is reduced. This reduction in connective tissue elasticity causes depressions at connective tissue anchor points. The result is a mottled, dimpled and lumpy appearance of the skin. Cellulites tend to gather, especially around the hips of females and the waists of males.

Masseurs more and more have turned to mechanical massage devices to aid them in the manipulating the folds of skin and subcutaneous tissue in attempts to break down the fat causing the cellulite condition. In the past, the mechanical massage devices have been designed to manipulate the skin and the adipose tissue by drawing the skin and fat deposits away from the underlying tissue into the mechanical massage device using vacuum chambers. The manipulations, in theory, move and rearrange the cells of the dermis and the underlying layers of fat. The idea is to reduce the amount of subcutaneous fat stores. In the past, the mechanical massage devices have reduced the fat deposits and improved the texture of the cellulose-afflicted skin, but only after a great many treatments.

Accordingly, a preferred embodiment of the invention provides a mechanical massage device that significantly reduces the number of treatments necessary to successfully combat cellulites. Exemplary embodiments successfully eliminate or significantly reduce the cellulite effects, in some cases with only a single treatment.

SUMMARY OF THE INVENTION

According to an aspect of the present invention, a mechanical massage device is provided, which makes it possible to perform massages that are much more effective in reducing and combating cellulites. More particularly, a mechanical massage apparatus is provided comprising a housing containing at least one tissue manipulating element within the housing and extending therefrom that is used to stress and mobilize a subject's dermis and underlying adipose tissue, when the device is pressed against and moved along the surface of a subject to massage the subject. In the preferred aspect of the invention, the device further includes a radiant heat source for applying heat that passes through the dermis and impinges on underlying adipose tissue during the massage to more effectively combat the effect of the cellulite.

In one preferred embodiment of the invention, the elements within the housing and extending therefrom, comprise at least two elements, both arranged to extend on a single axis or on axes normal to the direction of motion of the device during the massage. In another preferred embodiment, at least two of the elements are arranged in tandem in the direction of motion of the massage device during massages.

In a preferred embodiment of the invention, the elements within the housing and extending therefrom comprise at least two coaxial spheres arranged to extend on an axis that is normal to the direction of motion of the mechanical massaging device during the massage treatment.

In another preferred aspect of the mechanical massaging device, at least one of the spheres is coupled to a drive motor, and thereby rotated on its axis.

In yet another preferred embodiment of the invention, the elements extending from the housing comprise at least a cylindrical roller, whose axis is generally perpendicular to the direction of movement of the massage device.

Whether the elements be rollers or spheres in accordance with an aspect of the invention, heat is applied during the massage through a separate radiant heat source, or alternatively or additionally the radiant heat source may be located within the elements, i.e. the spheres, or the roller or on the surface of the spheres or rollers.

In yet another preferred embodiment of the invention, the surfaces of the elements are irregular, so that the elements also further massage the top surface of the skin and tissue, so that the massage device tends to be self-propelled reducing the necessary effort of the masseur in moving the device.

Alternatively and/or additionally, in another preferred embodiment of the invention, the surfaces of the elements are smooth to minimize any pinching of the subject's skin.

It has been found that radiant heat applied during a massage penetrates below the skin to the adipose tissue and tends to homogenize the adipose tissue; thereby, reducing the cellulite in a much more efficient manner. In a preferred embodiment of the invention, the heat comprises radiant heat in the infra-red range. By controlling the wavelength of the radiation, the heat may be made to better penetrate the surface of the skin to heat the fat deposits with minimal heating of the dermis and epidermis.

A further preferred aspect of the invention includes vacuumizing the casing holding the axially-aligned spheres or the rollers. Thus, the inventive device includes a housing, with elements within the housing extending therefrom, and a vacuum pump for lowering the pressure within the housing. The pump may be within the housing, or the housing may be attached to a source of vacuum. Radiant heat is applied to the area of the skin being massaged during the massaging operation. The combination of the massaging elements, the vacuum and the radiant heat, efficiently causes the adipose tissue to homogenize, and therefore makes it easier to spread and thereby destroy the cellulites.

There is thus provided, in accordance with a preferred embodiment of the invention a massaging apparatus comprising at least one massaging element rotatable within a housing, and extending therefrom to manipulate a subject's tissue, when the apparatus is applied to the subject; and said apparatus further including a radiant heat source for applying heat to the tissue. Preferably, the radiant heat source provides radiant heat having a wavelength in the range of 600 nm to 1500 nm.

In a preferred embodiment of the invention, the at least one massaging element comprises at least one substantially spherical massaging element. Alternatively, the at least one massaging element comprises at least one substantially cylindrical massaging element.

In another preferred embodiment of the invention, the massaging apparatus, comprises at least two massaging elements and the at least two massaging elements are mounted on a single axis. Alternatively or additionally, the at least two massaging elements are mounted on two separate axes. Preferably, the two separate axes are aligned. Alternatively, preferably the two separate axes are in tandem. Preferably, the at least one massaging element is motor-driven. Preferably, the at least one massaging element is motor-driven using gear coupling between the motor and the axis. Alternatively or additionally, the at least one massaging element is motor-driven using belt coupling between the axis and the motor. Alternatively or additionally, the at least one massaging element is motor driven using friction coupling between the axis or the element and the motor.

Preferably, the radiant heat source for applying heat to the tissue is a separate heat source removed from the massaging elements. Alternatively or additionally, the radiant heat source is located in the at least one massaging element. Alternatively or additionally, the radiant heat source is within the axis of the at least one massaging element. Alternatively or additionally, the radiant heat source is within at least one axis of said at least two massaging elements. Alternatively or additionally, the radiant heat source is in an outer portion of the at least one massaging element. Alternatively or additionally, the radiant heat source is in an outer portion of the at least one of the at least two massaging elements.

In a preferred embodiment of the invention, a vacuum is included within the housing. Preferably, a nozzle is provided for applying vacuum to the housing.

In a preferred embodiment of the invention, the at least two massaging elements mounted on a single axis are spherical elements. Alternatively or additionally, the at least two massaging elements mounted on the axes in tandem are spherical elements or cylindrical elements. Preferably, the at least one massaging element has a smooth surface. Alternatively or additionally, the at least two massaging elements have smooth surfaces.

There is further provided a massaging apparatus comprising at least one massaging element within a housing and extending therefrom, for manipulating the subject's tissue; the massaging element being substantially spherical; and a motor being coupled to said at least one massaging element for rotating said at least one massaging element. Preferably, the massaging apparatus includes a radiant heat source for applying heat to the tissue. Preferably, the massaging apparatus comprises at least two massaging elements.

In a preferred embodiment of the invention, chain coupling is used to couple said motor to said at least one massaging element. Alternatively or additionally, belt coupling is used to couple the motor to said at least one massaging element. Alternatively or additionally, friction coupling is used to couple the motor to the at least one massaging element. Alternatively or additionally, gear coupling is used to couple said motor to said at least one massaging element.

In a preferred embodiment of the invention, the at least two massaging elements are mounted on a single axis. Alternatively, preferably the at least two massaging elements are mounted on two separate axes. Preferably, the two separate axes are aligned. Preferably, the two separate axes are connected. Alternatively, preferably the two separate axes are in tandem. Preferably, the at least one massaging element has irregular surfaces.

There is further provided massaging apparatus comprising at least one massaging element rotating within a housing and extending therefrom to manipulate a subject's tissue; and the apparatus includes a heat source providing radiant heat that substantially passes through the skin and heats the fat. Preferably, the radiant heat has a wavelength in the range of 600–1500 nm.

The invention and the advantages which it provides will be understood more clearly when considered in the light of the following description of some embodiments thereof taken in conjunction with the following drawings, in which:

DETAILED DESCRIPTION

Figure 1:
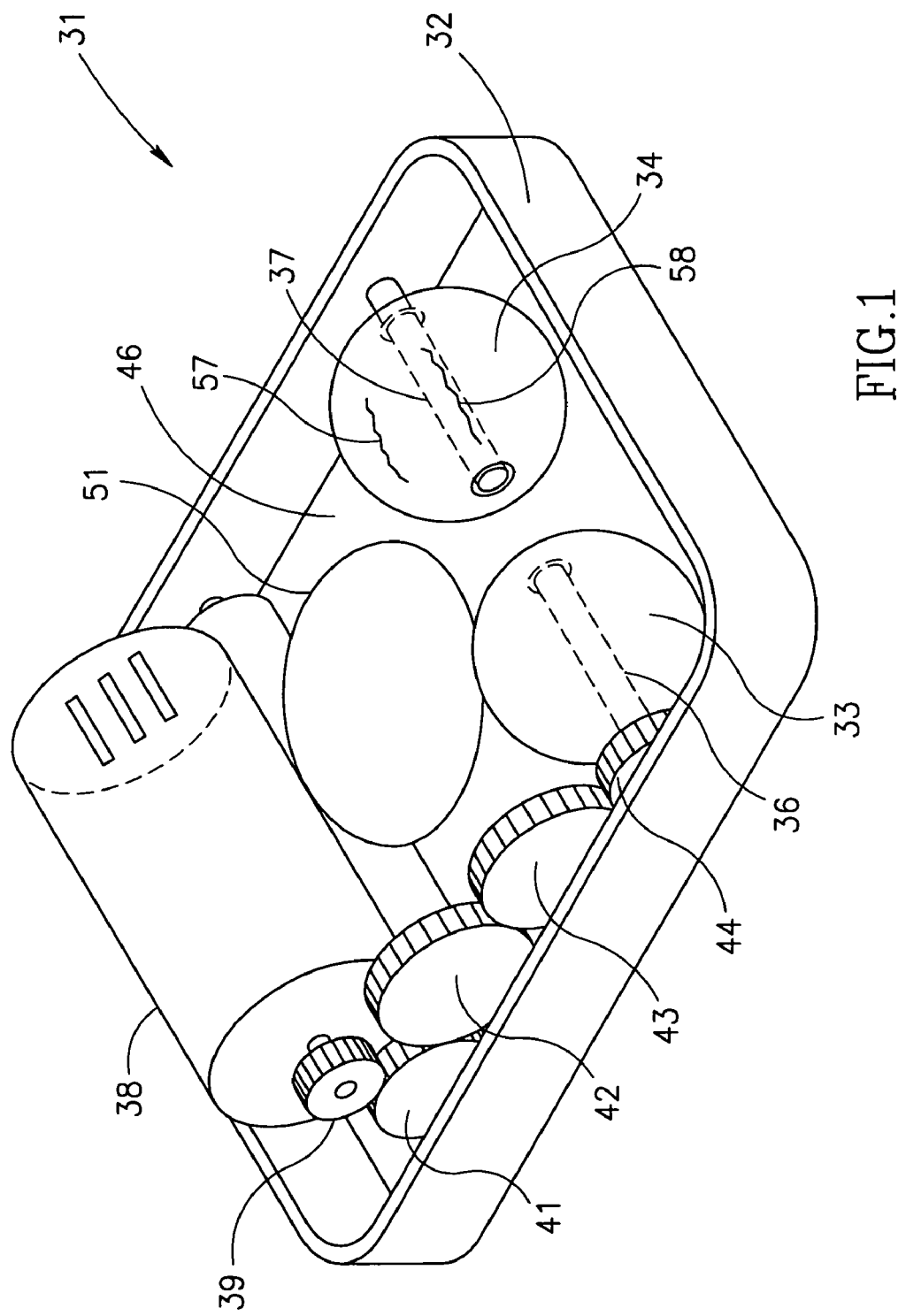
FIG. 1 is an illustration of the inventive massage device with the cover removed.

The massage device 31 as shown in FIG. 1 includes a housing, the bottom portion of which (i.e., the part closer to the skin of the patient) is shown at 32. The housing has within it, as shown, a visible pair of massaging elements, shown as spheres 33 and 34, which, in operation, are placed juxtaposed to the skin of the subject.

The masseur applies pressure, and moves the device to massage the subject, preferably aided by a motor 38. The spheres are shown as being axially mounted in a row on axes 36 and 37. The axes may be inter-linked so that both of the spheres are driven by the motor 38. The motor drives the drive gear 39, which in turn drives a series of gears 41, 42, 43 and 44. Gear 44 is attached to either axis 36 or both axes 36 and 37 to drive both spheres 33 and 34. Alternatively, a belt drive, a chain drive or a friction drive (not shown) may be used to rotate at least one of the elements.

The housing is connected to a vacuum source. Alternatively, the motor 38 can include a vacuum pump. Preferably, the housing is connected to a vacuum source, which lowers the air pressure in the vacuum area 46. Because of the lower pressure, the subject's dermal and sub-dermal tissue is drawn toward the vacuum area as the device is manipulated by the masseur over the patient's skin. In a preferred embodiment, the vacuum specifications were a maximum flow rate of up to 10 cubic ft./min. at 22 inches of mercury.

In a preferred embodiment of the invention, radiant heat is applied during the massage. The heat source is shown as the heat lamp 51 which heats the tissue being operated on by the massaging device. The heating, in combination with the manipulation, homogenizes the adipose tissue. It is build-up of fat that is the major cause of the reduction in elasticity of the skin at the adipose tissue which, in turn, causes depressions at the connective tissue anchor points, and results in the cellulite condition. Preferably, the heat source is an infra-red radiation source (in the 600 nm to 1500 nm range) that produces radiation that passes through the skin and heats the fat. Additionally or alternatively (in some preferred embodiments of the invention) the rollers contain the radiant heat source.

Figure 2A:
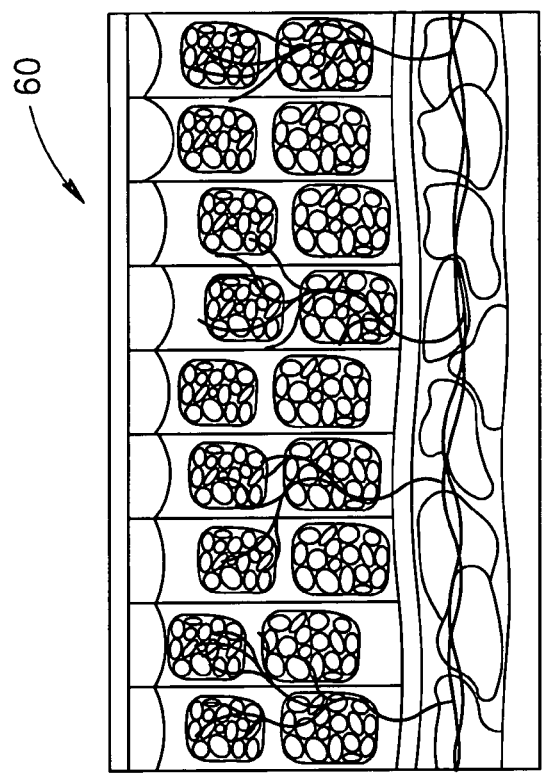
FIG. 2A is a showing of the cellulite formation prior to massaging with the inventive massage device.
Figure 2B:
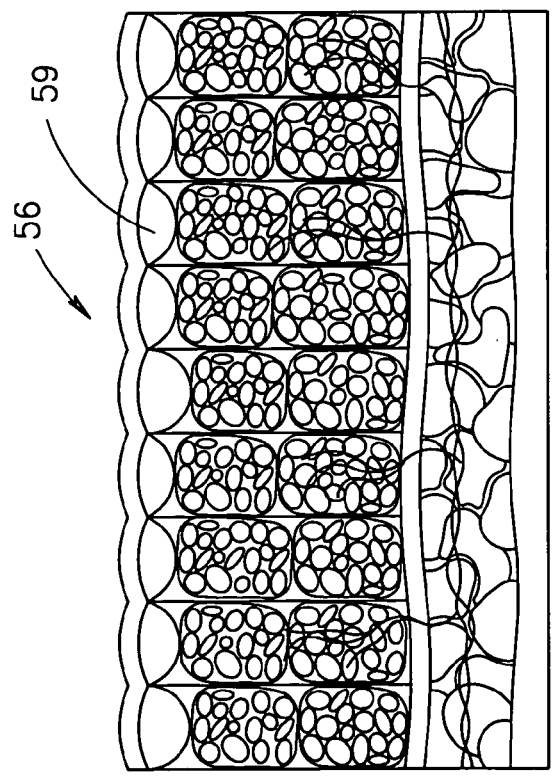
FIG. 2B shows a cellulite formation after massages with the inventive massage device.

The cellulite-afflicted skin 56 is shown with the underlying fat tissue 59 in FIG. 2A. FIG. 2B shows how the cellulite condition is removed due to the manipulation of the heated adipose tissue. The consequent homogenization due to manipulation of the heated fat tends to move the fat and spread it evenly as shown at 60. This restores the elasticity of connecting tissue and removes the depressions at the connective tissue anchor points.

It should be understood that radiant heating elements could alternatively or additionally be mounted right in the outer shell portion of the elements, such as shown at 57 on sphere 34. Alternatively or additionally, heating elements could be placed within the axis of the massage device element, such as within axis 37 of the sphere, as shown at 58 in FIG. 1. When the heating element is in the axis or in the shell, then preferably the sphere is fabricated from a heat-resistant material that is transparent to the radiation of the source. Preferably, the wavelength of the radiation is only minimally absorbed by the dermis and is transmitted through the epidermis and dermis to heat the fat tissue. When the heating coil is in the shell of the elements, then it is powered using slip rings in any manner known to those skilled in the art.

In a preferred embodiment of the invention, the outer surfaces of the spheres are irregular. This enables the device to be mobile and move under its own power, which greatly aids the masseur in providing the massage, as well as providing additional skin manipulation.

The spheres 33, 34 are shown in FIG. 1. The massage elements could also be arranged axially, as shown in FIG. 1, or the elements could be mounted on different tandem axes, spaced apart from each other, such as illustrated in FIG. 3B. Combinations of axially mounted elements and tandem mounted elements are within the scope of some preferred embodiments of the invention.

While the tandem massage elements 33 and 34 are shown positioned relatively closely spaced apart in FIG. 3B, within the scope of the invention element 34 could be positioned further from element 33. The heat lamp 51 and motor 38 could be moved closer to element 33, then element 34 could be positioned on the far side of motor 38. Power may be coupled to the massage device as shown at power line 50 in FIGS. 3A, 3B. Alternatively, rechargeable batteries could be used as the power source. Preferably, the housing restricts the volume of its interior to insure the efficiency of the vacuum.

Figure 3A:
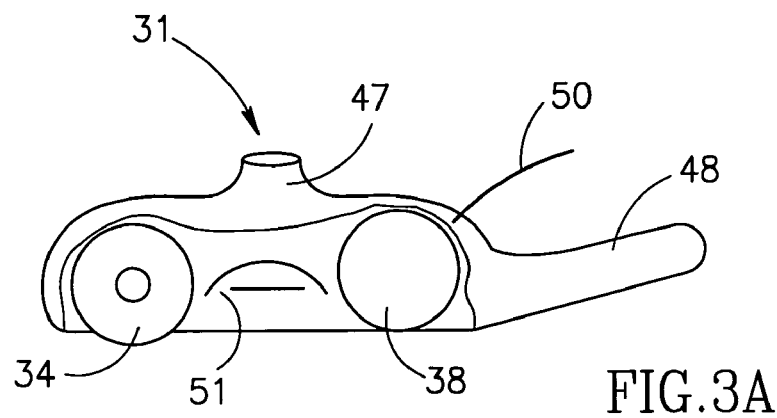
FIG. 3A is a side view of the massage device with a portion of the housing removed showing a massaging element and other parts within the device.
Figure 3B:
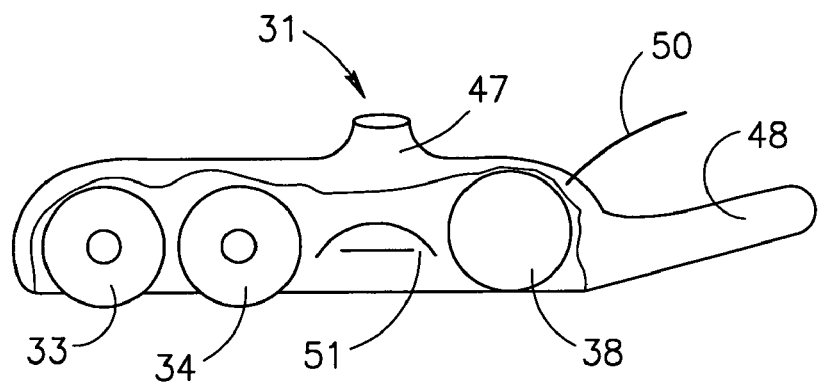
FIG. 3B is a side view of the massage device with massaging elements in tandem.

In FIGS. 3A and 3B, a connector or nozzle for connecting the housing to a vacuum source is indicated at 47. A handle 48 is provided on the device. The handle facilitates the moving and pressing down on the device during a massage. A breakaway section of the housing enables viewing in FIG. 3A one of the massaging elements 34, and the motor 38, which drives the spheres. A heat lamp 51, providing radiant heat, is also indicated in this view. FIG. 3A is thus a side view of the arrangement of the device of FIG. 1, where the massaging elements are mounted axially, while FIG. 3B shows the tandem mounting of the massaging elements.

Preferably, the housing has flaps (not shown) which extend to the surface of the skin and act to maintain the vacuum in the housing.

Figure 4:
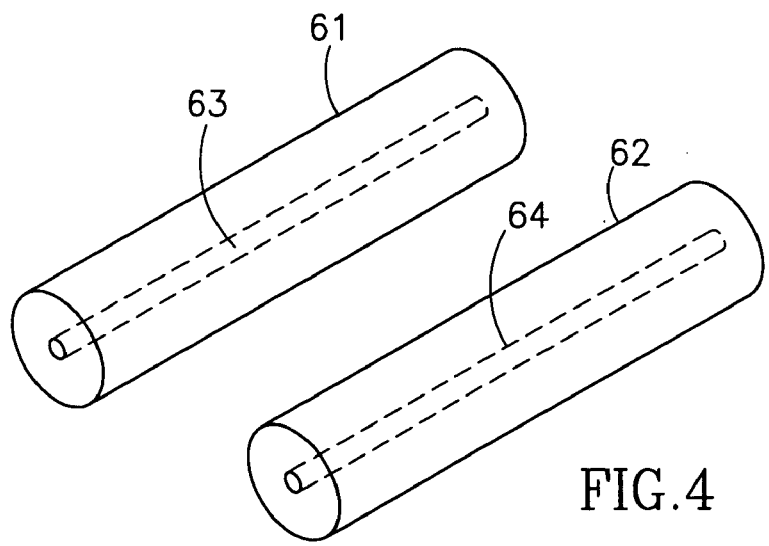
FIG. 4 is a pictorial showing of two cylindrical roller type massaging elements mounted in tandem.

The massage device elements could also be cylindrical rollers such as shown in FIG. 4, removed from the housing at 61 and 62. While two tandemly arranged rollers are shown, it should be understood that the rollers could also be arranged axially or a single roller could be used within the scope of the invention. The rollers are shown with axially-mounted heating elements 63 and 64.

The massage device, therefore, includes at least an element which extends from the vacuumized and heated housing or casing, enabling the elements to be movably pressed against the skin to manipulate the dermal and subcutaneous tissue of the patient. The manipulation of the skin and subcutaneous tissue is abetted since the skin and tissue are also being stressed by the vacuum. The manipulation and stressing in combination with the radiant heating homogenizes the fat tissue. The at least one massaging element is preferably motorized. The surface of the at least one massaging element is smooth. In preferred embodiments, the at least one massaging element is a sphere or ball fabricated from metal. Alternatively or additionally, the at least one massaging element is sphere or a cylinder fabricated from or coated with a plastic such as but not limited to Teflon.

A heat source is provided. The heat source can be separately located, such as the heating lamp 51. Alternatively or additionally, a heat source providing radiant heat can be located within the elements or on the surfaces of the elements themselves. The elements can have shapes including, but not limited to spheres or rollers. The axially-aligned spheres are found to manipulate more tissue per area traversed by the massage device than the prior art's cylindrical rollers arranged in parallel.

It should be apparent that the embodiment described herein is merely exemplary, and that a person skilled in the art may make many variations and modifications to the embodiments as described herein. Any and all such variations or modifications, as well as other, which may become apparent to those skilled in the art, are intended to be included within the scope of the invention as defined by the appended claims.

The terms "include", "comprise" and "have" and their conjugates, as used herein mean "including but not necessarily limited to."

What is claimed is:

1. A method for reducing effects on appearance of a region of a person's skin resulting from cellulite tissue deposits underlying the skin region, comprising:

providing an apparatus for treating cellulite tissue underlying a skin region comprising:
   a housing,
   a vacuum element that generates a negative pressure region within said housing, said negative pressure region being operative to draw the region of skin and the underlying cellulite tissue towards said housing when said apparatus is applied to the skin region,
   at least one tissue manipulating element positioned within said housing and extending from said housing so that said at least one tissue manipulating element is positioned to stress and mobilize the skin region and the underlying cellulite tissue when said apparatus is used to massage the skin region, and
   a radiant heat source mounted to said housing that provides radiant heat operative to heat the cellulite tissue when said apparatus is applied to the skin region;

drawing the region of skin and the underlying cellulite tissue towards said housing using said vacuum element;

applying radiant heat from said radiant heat source to the skin region such that the radiant heat substantially passes through the skin and heats the underlying cellulite tissue;

the step of applying radiant heat comprising applying to the skin region, light having a wavelength in the range of 600 nm to 1500 nm; and homogenizing the cellulite tissue underlying the skin region by stressing and mobilizing the skin region and the underlying cellulite tissue by using said at least one tissue manipulating element to massage the skin region.

2. The method according to claim 1 wherein said at least one tissue manipulating element within said apparatus comprises at least one substantially spherical element.

3. The method according to claim 1 wherein said at least one tissue manipulating element within said apparatus comprises at least one substantially cylindrical element.

4. The method according to claim 1 wherein said at least one tissue manipulating element within said apparatus comprises at least two tissue manipulating elements.

5. The method according to claim 4 wherein said at least two tissue manipulating elements within said apparatus are mounted on a single axis.

6. The method according to claim 4 wherein the at least two tissue manipulating elements within said apparatus are mounted on two separate axes.

7. The method according to claim 1 wherein the at least one tissue manipulating element within said apparatus is motor-driven.

8. The method according to claim 1 wherein said radiant heat source within said apparatus is a separate heat source removed from the at least one tissue manipulating element.

9. The method according to claim 1 wherein the radiant heat source within said apparatus is located within the at least one tissue manipulating element.

10. The method according to claim 9 wherein the radiant heat source is in an outer portion of the at least one tissue manipulating element.

11. The method according to claim 9 wherein the radiant heat source within said apparatus is within an axis of the at least one tissue manipulating element.

12. The method according to claim 1 wherein the step of applying radiant heat comprises applying radiant heat from said radiant heat source to the region of skin drawn towards said housing by said vacuum element.

13. The method according to claim 12 wherein the step of applying radiant heat comprises controlling the wavelength of the radiant heat from said radiant heat source so as to heat the cellulite tissue underlying the skin while only minimally heating the skin.

14. The method according to claim 12 wherein the step of applying radiant heat comprises controlling the wavelength of the radiant heat from said radiant heat source so that the cellulite tissue underlying the skin rises to a temperature above that of the skin.

15. The method according to claim 1 wherein the step of homogenizing the cellulite tissue underlying the skin region comprises stressing and mobilizing the skin region and the underlying cellulite tissue that have been drawn towards said housing using said vacuum element.

16. The method according to claim 1 wherein the step of homogenizing the cellulite tissue underlying the skin region comprises stressing and mobilizing the skin region and the underlying cellulite tissue that have been heated by said radiant heat source.

17. The method according to claim 1 wherein the step of homogenizing the cellulite tissue underlying the skin region comprises stressing and mobilizing the skin region and the underlying cellulite tissue while the skin region and the underlying cellulite tissue are being drawn towards said housing using said vacuum element and while the skin region and the underlying cellulite tissue are being heated by said radiant heat source.

18. The method according to claim 1 wherein the step of homogenizing the cellulite tissue underlying the skin region comprises stressing and mobilizing the skin region and the underlying cellulite tissue such that the cellulite tissue underlying the skin region is moved and spread evenly.

* * * * *